United States Patent [19]

Williams, III et al.

[11] 4,136,087

[45] Jan. 23, 1979

[54] METHOD FOR MAKING AROMATIC CYCLIC POLYFORMALS

[75] Inventors: Frank J. Williams, III, Scotia; Paul E. Donahue, Schenectady, both of N.Y.

[73] Assignee: General Electric Company, Schenectady, N.Y.

[21] Appl. No.: 905,636

[22] Filed: May 15, 1978

[51] Int. Cl.² .............................................. C08G 65/40
[52] U.S. Cl. .................................... 528/219; 260/338; 528/493
[58] Field of Search .......................... 260/61, 47 R, 49

[56] References Cited

U.S. PATENT DOCUMENTS 3,069,386 12/1962 Barclay, Jr. ............................ 260/49

*Primary Examiner*—Lester L. Lee
*Attorney, Agent, or Firm*—William A. Teoli; Joseph T. Cohen; Charles T. Watts

[57] ABSTRACT

A method is provided for making aromatic cyclic polyformals by effecting reaction between a methylene halide and an anhydrous bisphenol dianion, followed by a precipitation and an extraction of the resulting aromatic polyformal reaction product. The aromatic cyclic polyformals can be used as plasticizers for organic polymers for making wire coating formulations.

6 Claims, No Drawings

METHOD FOR MAKING AROMATIC CYCLIC POLYFORMALS

BACKGROUND OF THE INVENTION

The present invention relates to a method of making aromatic cyclic polyformals of the formula

 (1)

where R is a divalent aromatic $C_{(6-30)}$ organic radical defined more particularly below and n is an integer equal to from 2-25 inclusive. More particularly, the present invention relates to the extraction of aromatic cyclic polyformal from aromatic polyformal formed by reacting a bisphenol dianion with a methylene halide.

An alternative method of making the aromatic cyclic polyformal of formula (1) is shown in copending application Ser. No. 905,637 of Donald S. Johnson, A Method For Making Cyclic Polyformals, filed concurrently herewith and assigned to the same assignee as the present invention. In Ser. No. 905,637, a phase transfer catalyst is used to effect reaction between an insitu formed bisphenol dianion in an aqueous phase with a methylene halide organic phase to directly produce aromatic cyclic polyformal of formula (1), substantially free of aromatic linear polyformal.

In copending application Ser. No. 905,637, of Allan S. Hay, for Cyclic Polyformals and Method For Making, also filed concurrently herewith and assigned to the same assignee as the present invention, cyclic polyformals of 2,2-bis(4-hydroxyphenyl)-1,1-dichloroethylene, or "dichloride", is described. Isolation of the cyclic polyformal of the dichloride is achieved by the use of a high pressure liquid chromatograph.

STATEMENT OF THE INVENTION

The present invention is based on the discovery that an aromatic cyclic polyformal of formula (1) can be made by preforming a dianion of a bisphenol of the formula,

HO—R—OH, (2)

where R is as previously defined, in a mixture of alkali metal hydroxide, dipolar aprotic solvent and an azeotropic aromatic hydrocarbon solvent to produce an anhydrous heterogeneous bisphenol-dianion mixture which is combined with methylene halide, followed by a precipitation and an extraction step.

There is provided, a method for making aromatic cyclic polyformal which comprises, (1) stirring a mixture at a temperature of from 25° C. to 80° C. comprising, (a) a methylene halide and (b) an anhydrous bisphenol dianion formed by refluxing and azeotroping a mixture of an alkali metal hydroxide, and a bisphenol, in the presence of a mixture of a dipolar aprotic solvent and an aromatic hydrocarbon azeotroping solvent, where there is used from 1 to 100 moles of methylene halide per mole of bisphenol dianion and (2) adding the resulting mixture of (1) to a precipitating solvent, (3) recovering aromatic polyformal from (2) and (4) thereafter extracting with a dialkyl ketone aromatic cyclic polyformal from the aromatic polyformal of (3).

Radicals included by R of formulas (1) and (2) are, for example, phenylene, tolylene, xylylene, naphthalene, etc.; halogenated derivatives of such divalent aromatic hydrocarbon radicals, such as chlorophenylene, bromotolylene, etc., divalent radicals, such as —$R^1$Q-$R^1$—, where Q can be cyclohexyl, fluorenyl, —O—, —S—,

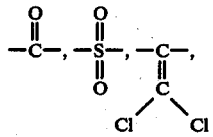

$R^1$ is selected from $C_{(6-13)}$ R radicals, —$C_yH_{2y}$—, and y is equal to 1 to 5 inclusive.

Some of the bisphenols of formula (2), are compounds such as:

2,2-bis(4-hydroxyphenyl)propane (bisphenol-A);
2,4'-dihydroxydiphenylmethane;
bis-(2-hydroxyphenyl)methane;
1,1-bis(4-hydroxyphenyl)ethane;
1,1-bis-(4-hydroxyphenyl)propane;
3,3-bis-(4-hydroxyphenyl)pentane;
4,4'-dihydroxybiphenyl;
4,4'-dihydroxy-3,3',5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenylsulfide;
hydroquinone;
resorcinol;
3,3-bis(4-hydroxyphenyl)-fluorene;
3,4'-dihydroxydiphenylmethane;
4,4'-dihydroxybenzophenone;
4,4'-dihydroxydiphenylether;
1,1-dichloro-2,2-bis(4-hydroxyphenyl)ethylene, and
1,1,1-trichloro-2,2-bis(4-hydroxyphenyl)ethane.

Methylene halides which can be used in the practice of the invention, are, for example, methylene chloride, methylene bromide, chlorobromo methane, etc. Alkali hydroxides which can be employed in the practice of the invention are, for example, potassium hydroxide which can be in the form of pellets, powder, etc., sodium hydroxide, etc.

Dialkyl ketones which can be employed in the practice of the present invention are ketones having $C_{(1-4)}$ alkyl groups which can be the same or different, such as acetone, methylethyl ketone, diethyl ketone, methylpropyl ketone, etc. Azeotroping aromatic organic hydrocarbon solvents which can be employed are, for example, toluene, xylene, benzene, etc. Dipolar aprotic solvents which can be used to make the bisphenol dianion are, those stable to hydrolysis, for example, dimethylsulfoxide, sulfolane, etc.

In the practice of the invention, a mixture of the bisphenol, aqueous alkali metal hydroxide, aromatic hydrocarbon solvents and dipolar aprotic solvents is refluxed under nitrogen or other inert gas; the water is completely separated from the mixture and the aromatic hydrocarbon solvent can then be distilled and the residue allowed to cool to room temperature. At least stoichiometric amounts of the alkali metal hydroxide is employed to completely react with the bisphenol. There is then added to the bisphenol dianion in the form of a heterogeneous mixture, greater than 1 mole of methylene halide per mole of the bisphenol dianion. The resulting mixture is then stirred until the bisphenol dianion has been completely reacted, as shown by the absence of bisphenol, using a high pressure liquid chromatograph. During the reaction, the mixture may be heated to facilitate the displacement. The reaction mixture is then added to a precipitating solvent, for example, methanol, water, etc., and the resulting mixture thoroughly agitated. Aromatic polyformal is then recovered by standard techniques, such as filtration, decantation, centrifuging, etc.

The aromatic polyformal can then be extracted with a dialkyl ketone by standard techniques, such as placing the aromatic polyformal in a Soxhlet extractor and having the aromatic polyformal exposed to refluxing acetone. The aromatic cyclic polyformal is then recovered as an extract from the dialkyl ketone.

As shown in copending application Ser. No. 889,393, of Allan S. Hay, for Method For Making Polyformals and Polyformal Products Made Thereby, filed Mar. 23, 1978 and assigned to the same assignee as the present invention, the aromatic cyclic polyformal made by the method of the present invention can be used to make wire coating formulations when combined with an appropriate organic solvent and a Lewis Acid catalyst. In addition, the aforementioned aromatic cyclic polyformal can be employed as plasticizers in a variety of organic polymers, such as a polycarbonate, polyester, etc.

In order that those skilled in the art will be better able to practice the invention, the following examples are given by way of illustration and not by way of limitation. All parts are by weight.

EXAMPLE 1

A mixture of 45.35 parts of 2,2-bis(4-hydroxyphenyl) propane, 31.79 parts of 50% aqueous sodium hydroxide, about 180 parts of toluene and about 180 parts of dimethylsulfoxide was refluxed under nitrogen. During refluxing, water was continuously azeotroped from the mixture. When the mixture was dried, the toluene was removed by distillation and the mixture was then allowed to cool to room temperature. There was obtained a heterogeneous mixture of bisphenol-A dianion. There was added about 96 parts of methylene chloride to the bisphenol-A dianion and the resulting mixture was heated at 77°–78° C. for 5 hours. The mixture was then added to methanol in a blender and thoroughly agitated. The product was isolated by filtration and then dried. There was obtained 42.3 parts of an aromatic polyformal based on method of preparation. The aromatic polyformal had an intrinsic viscosity of 0.38 and contained 66% by weight of aromatic cyclic polyformal having the formula

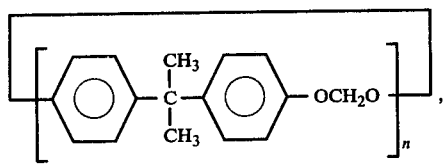

where n is an integer equal to 2–25 inclusive.

The above aromatic polyformal was extracted with acetone and greater than 70% of the cyclics present were recovered by concentration of the acetone solution.

EXAMPLE 2

The procedure of Example 1 was repeated. During the extraction step, acetone was refluxed through the system for 16 hours. As the extraction continued, a solid began to separate from the acetone solution. This solid was isolated by filtration to give 6.61 parts of material which was found to be the cyclic dimer having the formula,

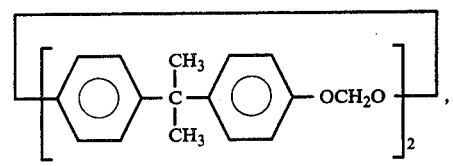

and the cyclic tetramer having the formula,

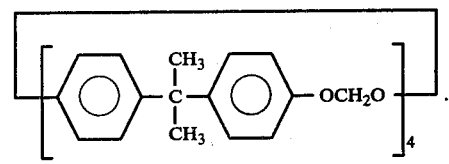

The remainder of the cyclics were obtained by concentration of the acetone filtrate.

There was added a diethylether-$BF_3$ complex to a concentrated methylene chloride solution of the above polyformal dimer to produce a 1% by weight complex solution. The mixture was stirred with a metal spatula. A solvent resistant coating was found on the metal spatula after it was removed from the mixture and allowed to air dry. A cross-linking of the dimer had occurred which was confirmed by NMR.

EXAMPLE 3

A mixture of 40.18 parts of 4,4'-dihydroxydiphenol ether, 31.79 parts of 50% aqueous sodium hydroxide, 180 parts of toluene and 180 parts of dimethylsulfoxide is treated as described in Example 1 to give a heterogeneous solution of the anhydrous disodium salt of 4,4'-dihydroxydiphenyl ether in dimethylsulfoxide. To this solution is added 40 parts of methylene chloride and the mixture is heated at 50°0 C. for 7 hours. The reaction mixture is cooled to 25° C. and added to methanol to precipitate the aromatic polyformal. This product has an intrinsic viscosity of 0.35 and contains 40% by weight of aromatic cyclic polyformal having the formula,

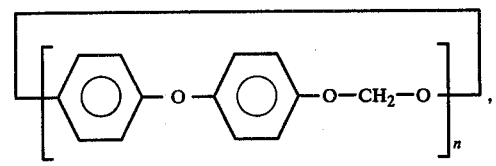

where n is an integer equal to 2–25 inclusive. The cyclic polyformal can be removed from the linear polyformals by extraction with methylethyl ketone.

Although the above examples are directed to only a few of the very many variables of the method of the present invention, it should be understood that the method of the present invention is directed to the production of a much broader variety of aromatic cyclic polyformals shown by formula (1), based on the use of the bisphenol of formula (2), in combination with alkali metal hydroxide and methylene halide, etc., as shown in the description preceding these examples.

What we claim as new and desire to secure by Letters Patent of the United States is:

1. A method for making aromatic cyclic polyformal which comprises,
    (1) stirring a mixture at a temperature of from 25° C. to 80° C. comprising
        (a) methylene halide and
        (b) the anhydrous bisphenol dianion formed by refluxing and azeotroping a mixture of an alkali metal hydroxide, and a bisphenol, in the presence of a mixture of a dipolar aprotic solvent and an aromatic hydrocarbon azeotroping solvent,
    where there is used from 1 to 100 moles of methylene halide, per mole of bisphenol dianion and
    (2) adding the resulting mixture of (1) to a precipitating solvent,
    (3) recovering aromatic polyformal from (2) and
    (4) thereafter extracting with a dialkyl ketone aromatic cyclic polyformal from the aromatic polyformal of (3).

2. The method of claim 1, where the bisphenol is 2,2-bis(4-hydroxyphenyl)propane.

3. The method of claim 1, where the aromatic hydrocarbon solvent is toluene.

4. The method of claim 1, where the dipolar aprotic solvent is dimethylsulfoxide.

5. The method of claim 1, where the alkali metal hydroxide is sodium hydroxide.

6. The method of claim 1, where the bisphenol is 4,4'-dihydroxydiphenyl ether.

* * * * *